United States Patent [19]

Freidinger

[11] Patent Number: 5,089,638
[45] Date of Patent: Feb. 18, 1992

[54] AMINO ACID ANALOGS AS CCK-ANTAGONISTS

[75] Inventor: Roger M. Freidinger, Hatfield, Pa.

[73] Assignee: Merck & Co., Inc., Rahway, N.J.

[21] Appl. No.: 400,608

[22] Filed: Aug. 30, 1989

Related U.S. Application Data

[62] Division of Ser. No. 874,928, Jun. 16, 1986, Pat. No. 4,880,938.

[51] Int. Cl.$^5$ ............................................. C07D 307/82
[52] U.S. Cl. ..................... 549/468; 548/492; 548/571; 548/483; 549/462; 549/436; 549/57; 546/192; 546/225; 546/168; 544/106; 564/169; 564/183
[58] Field of Search ........................................ 549/468

[56] References Cited

U.S. PATENT DOCUMENTS 4,515,803  5/1985  Henning et al. .................... 514/338

FOREIGN PATENT DOCUMENTS

| 0272228 | 6/1988 | European Pat. Off. . |
| WO86/03489 | 6/1986 | PCT Int'l Appl. . |
| WO86/03968 | 7/1986 | PCT Int'l Appl. . |
| WO87/03869 | 7/1987 | PCT Int'l Appl. . |
| 2160869A | 1/1986 | United Kingdom . |

*Primary Examiner*—David B. Springer
*Attorney, Agent, or Firm*—Mark R. Daniel; Hesna J. Pfeiffer

[57] ABSTRACT

Analogs of glutamic acid and related amino acids and pharmaceutically-acceptable salts thereof which antagonize the function of cholecystokinins and gastrin disease states in animals and compositions for and methods of preventing or treating disorders of the gastrointestinal, central nervous and appetite regulatory systems of mammals, especially of humans.

5 Claims, No Drawings

AMINO ACID ANALOGS AS CCK-ANTAGONISTS

This is a division of application Ser. No. 874,928, filed June 16, 1986 now U.S. Pat. No. 4,890,938.

BACKGROUND OF THE INVENTION

Cholecystokinins (CCK) are neuropeptides which include CCK-33, a neuropeptide of thirty-three amino acids in its originally isolated form (see, Mutt and Jorpes, Biochem. J. 125. 678 (1971)), its carboxylterminal octapeptide, CCK-8 (a naturally-occurring neuropeptide, also, and the minimum fully active sequence), and 39- and 12-amino acid forms. CCK's are believed to be physiological satiety hormones and, therefore, may play an important role in appetite regulation (G. P. Smith, Eating and Its Disorders, A. J. Stunkard and E. Stellar, Eds., Raven Press, New York, 1984, p. 67).

Gastrin occurs in 34-, 17- and 14-amino acid forms in circulation and is related to CCK by identity of the C-terminal pentapeptides Gly-Trp-Met-Asp-Phe-NH$_2$. Both gastrin and CCK exist in gastrointestinal tissue and in the central nervous system (see, V. Mutt, Gastrointestinal Hormones, G. B. J. Glass, Ed., Raven Press, N.Y., 1980, p. 169 and G. Nisson, ibid. p. 127).

Among additional effects, CCK's stimulate colonic motility, gall bladder contraction, pancreatic enzyme secretion, and inhibit gastric emptying. CCK's reportedly co-exist with dopamine in certain mid-brain neurons and thus may also play a role in the functioning of dopaminergic systems in the brain, as well as serving as neurotransmitters in their own right. See: A. J. Prange et al., "Peptides in the Central Nervous System", Ann. Repts. Med. Chem. 17, 31, 33 (1982) and references cited therein; J. A. Williams, Biomed. Res. 3 107 (1982); and J. E. Morley, Life Sci. 30, 479, (1982). The primary role of gastrin appears to be stimulation of the secretion of water and electrolytes from the stomach, and, as such, it is involved in control of gastric acid secretion.

Antagonists to CCK have been useful for preventing and treating CCK-related disorders of the gastrointestinal, central nervous and appetite regulatory systems of animals, especially of humans. CCK antagonists are also useful in potentiating and prolonging opiate-mediated analgesia and thus have utility in the treatment of pain [see P. L. Faris et al., Science 226, 1215 (1984)]. Gastrin antagonists are useful in the treatment and prevention of gastrin-related disorders of the gastrointestinal system in humans and animals, such as ulcers, Zollinger-Ellison syndrome, antral G cell hyperplasia and other conditions, in which reduced gastrin activity is of therapeutic value. CCK and gastrin also have trophic effects on certain tumors [K. Ohyama, Hokkaido J. Med. Sci., 60, 206–216 (1985)], and antagonists of CCK and gastrin are useful in treating these tumors [see, R. D. Beauchamp et al, Ann. Surg., 202, 303 (1985)].

Three distinct chemical classes of CCK-receptor antagonists have been reported. The first class comprises derivatives of cyclic nucleotides, of which dibutyryl cyclic GMP has been shown to be the most potent by detailed structure-function studies (see, N. Barlos et al., Am. J. Physiol,. 242, G 161 (1982) and P. Robberecht et al., Mol. Pharmacol. 17, 268 (1980)). The second class comprises peptide antagonists which are C-terminal fragments and analogs of CCK, of which both shorter (Boc-Met-Asp-Phe-NH$_2$, Met-Asp-Phe-NH$_2$), and longer (Cbz-Tyr(SO$_3$H)-Met-Gly-Trp-Met-Asp-NH$_2$) C-terminal fragments of CCK can function as CCK antagonists, according to recent structure-function studies (see, R. T. Jensen et al., Biochem Biophys. Acta., 757, 250 (1983, and M. Spanarkel et al.. J. Biol. Chem., 258, 6746 (1983)). The latter compound was recently reported to be a partial agonist [see, J. M. Howard et al., Gastroenterology 86(5) Part 2, 1118 (1984)]. Then, the third class of CCK-receptor antagonists comprises the amino acid derivatives: proglumide, a derivative of glutaramic acid, and the N-acyl tryptophans including para-chlorobenzoyl-L-tryptophan (benzotript), [see, W. F. Hahne et al., Proc. Natl. Acad. Sci. U.S.A., 78, 6304 (19811), and R. T. Jensen et al., Biochem. Biophys. Acta., 761, 269 (1983)]. All of these compounds, however, are relatively weak antagonists of CCK (IC$_{50}$: generally 10$^{-4}$M (although more potent analogs of proglumide have been recently reported in F. Makovec et al., Arzneim-Forsch Drug Res., 35 (II), 1048 (1985) and in German Patent Application DE 3522506A1), but down to 10$^{-6}$M in the case of peptides), and the peptide CCK-antagonists have substantial stability and absorption problems.

In addition, improved CCK-antagonists comprising a nonpeptide of novel structure from fermentation sources [R. S. L. Chang et al. Science, 230, 177–179 (1985)]and 3-substituted benzodiazepines based on this structure [published European Patent Applications 0 167 919, 0 167 920 and 0 169 392] have also been reported.

No really effective receptor antagonists of the in vivo effects of gastrin have been reported (J. S. Morley, Gut Pept. Ulcer Proc., Hiroshima Symp. 2nd, 1983, p. 1), and very weak in vitro antagonists, such as proglumide and certain peptides have been reported [J. Martinez, J. Med. Chem. 27, 1597 (1984)]. Recently, however, pseudopeptide analogs of tetragastrin have been reported to be more effective gastrin antagonists than previous agents [J. Martinez et al., J. Med. Chem., 28, 1874–1879 (1985)].

It was, therefore, an object of this invention to identify substances which more effectively antagonize the function of cholecystokinins in disease states in mammals, especially in humans. It was another object of this invention to prepare novel compounds which inhibit cholecystokinins and antagonize the function of gastrin. It was still another object of this invention to develop a method of antagonizing the functions of cholecystokinin/ gastrin in disease states in mammals. It is also an object of this invention to develop a method of Preventing or treating disorders of the gastrointestinal, central nervous and appetite regulatory systems of mammals, especially of humans.

DESCRIPTION OF THE INVENTION

The present invention is directed to analogs of glutamic acid and related amino acids of the formula:

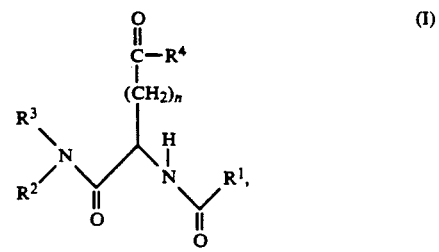

wherein:

$R^1$—$(CH_2)_m$—$R^5$ or $X^1$—$(CH_2)_m$—$R^6$;

$R^2$ and $R^3$ are independently selected from H; $C_1$-$C_8$-straight- or branched-chain-alkyl; $C_3$-$C_8$-cycloalkyl; phenyl; benzyl; mono- or dihalophenyl; and mono- or dihalobenzyl; with the proviso that $R^2$ and $R^3$ may not both be H concurrently;

$R^4$ is OH; $C_1$-$C_4$-straight- or branched-chain-alkoxy; $C_3$-$C_6$-cycloalkoxy; $OCH_2$-phenyl; amino-mono- or di-$C_1$-$C_4$-straight- or branched-chain alkyl; amino-mono- or di-$C_3$-$C_6$-cycloalkyl; NH—$CH_2$-phenyl; piperidino; pyrrolidino; or morpholino;

$R^5$ is α- or β-naphthyl;

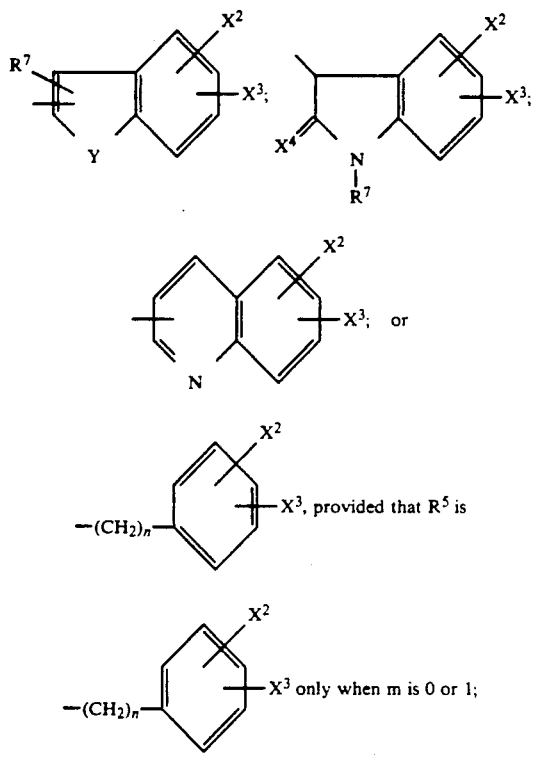

$R^6$ is α- or β-naphthyl;

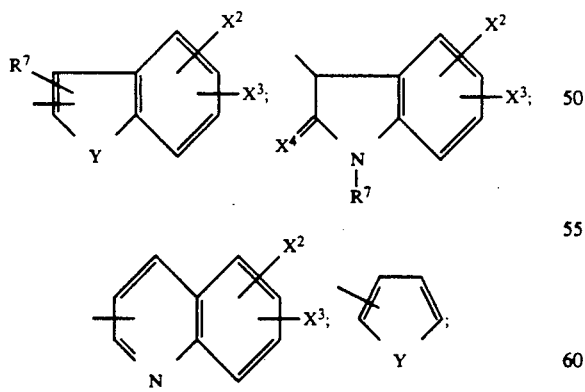

mono- or di-substituted- or unsubstituted-phenyl, where the substituent(s) is/are selected from halo; $NO_2$; OH; $CF_3$; CN; $C_1$-$C_4$-straight- or branched-chain-alkyl; $C_1$-$C_4$-straight- or branched-chain-alkyloxy; and $C_1$-$C_4$-straight- or branched-chain-alkylthio;

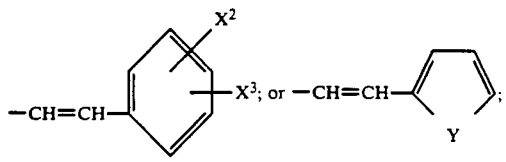

$R^7$ is H; $C_1$-$C_4$-straight- or branched-chain-alkyl;

$X^1$ is O or NH;

$X^2$ and $X^3$ are independently H; OH; $NO_2$; halo; $C_1$-$C_4$-straight- or branched-chain-alkyl; $C_1$-$C_4$-straight- or branched-chain-alkylthio; or $C_1$-$C_4$-straight- or branched-chain-alkoxy;

$X^4$ is O or HH;

Y is O, S, $CH_2$, or $NR^7$;

n is 1-to-3;

m is 0-to-4; and halo is F, Cl, Br, or I;

or pharmaceutically-acceptable salts of these compounds.

The stereochemistry of the compounds may be D, L or DL.

As used herein, "Boc" represents tert-butyloxycarbonyl, "Bzl" represents benzyl, "DCC" represents dicyclohexylcarbodiimide, "EDC" represents 1-(3-dimethylaminopropyl)-3-ethylcarbodiimide hydrochloride, "DPPA" represents diphenylphosphorylazide and "THF" represents tetrahydrofuran.

Preferred compounds according to the present invention are those wherein $R^2$ and $R^3$ are independently —$(CH_2)_{3-5}$—$CH_3$, benzyl or mono- or dihalobenzyl; $R^4$ is OH, $C_1$-$C_4$-straight- or branched-chain-alkoxy, $OCH_2$-phenyl, amino-mono- or di-$C_1$-$C_4$-straight- or branched-chain-alkyl, NH—$CH_2$-phenyl, piperidino, pyrrolidino or morpholino; $R^5$ is α- or β-naphthyl or

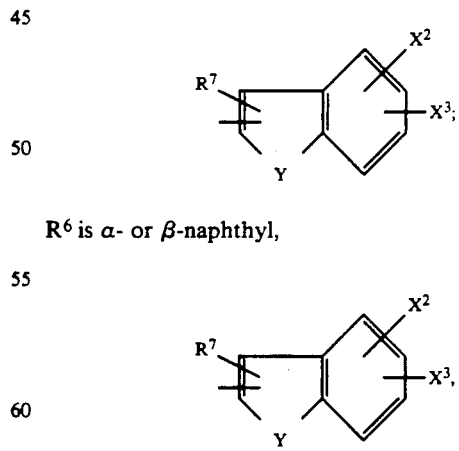

$R^6$ is α- or β-naphthyl, mono- or di-substituted or unsubstituted-phenyl (where the substituent(s) is/are selected from halo, $CF_3$, $C_1$-$C_4$-straight- or branched-chain-alkyl, $C_1$-$C_4$-straight- or branched-chain-alkoxy, and $C_1$-$C_4$-straight- or branched-chain-alkylthio),

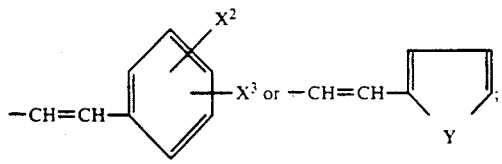

$R^7$ is H; $X^2$ and $X^3$ are independently H, halo, $C_1-C_4$-straight- or branched-chain-alkylthio or $C_1-C_4$-straight- or branched-chain alkoxy; Y is O or $NR^7$; n is 2 or 3; and m is 0 or 1. For preventing and treating CCK-related disorders, compounds wherein $R^1$ is $(CH_2)_m-R^5$; $R^2$ and $R^3$ are independently $(CH_2)_{3-5}-CH_3$; $R^4$ is OH; $R^5$ is α- or β-naphthyl or

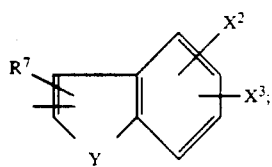

$R^7$ is H; $X^2$ and $X^3$ are independently H or halo; Y is $NR^7$; n is 2 and m is 0, are generally preferred. For preventing and treating gastrin-related disorders, compounds wherein $R^1$ is $X^1-(CH_2)_m-R^6$; $R^2$ and $R^3$ are independently $(CH_2)_{3-5}-CH_3$; $R^4$ is $C_1-C_4$-straight or branched-chain-alkoxy, $OCH_2$-phenyl, amino-mono- or di-$C_1-C_4$-straight-or branched-chain-alkyl, $NH-CH_2$-phenyl, piperidino, pyrrolidino or morpholino; $R^6$ is α- or β-naphthyl,

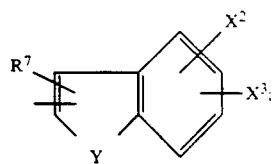

unsubstituted or mono- or disubstituted phenyl, where the substituent is halo, $C_1-C_4$-straight- or branched-chain-alkoxy, $C_1-C_4$-straight- or branched-chain-alkyl,

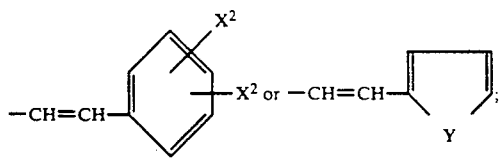

$R^7$ is H; $X^1$ is NH; $X^2$ and $X^3$ are independently H or halo; Y is $NR^7$; n is 2 or 3 and m is 0, are generally preferred.

Such preferred compounds include:
- (S)-5-(dipropylamino)-4-[(1H-indol-2-ylcarbonyl)amino]-5-oxo-pentanoic acid;
- (R)-5-(dipropylamino)-4-[(1H-indol-2-ylcarbonyl)amino]-5-oxo-pentanoic acid;
- (R)-5-(dipentylamino)-4-[(1H-indol-2-ylcarbonyl)amino]-5-oxo-pentanoic acid;
- (R)-5-(dipropylamino)-4-[(1H-indol-2-ylcarbonyl)amino]-5-oxo-1-(phenylmethoxy)-pentanoic acid;
- (RS)-4-[(4-chlorophenylaminocarbonyl)amino]-5-(dipentylamino)-5-oxo-pentanoic acid;
- (RS)-4-[(4-chlorophenylaminocarbonyl)amino]-5-(dipentylamino)-5-oxo-1-(phenylmethoxy)-pentanoic acid;
- (R)-5-(dicyclohexylamino)-4-[(1H-indol-2-ylcarbonyl)amino]-5-oxo-1-(phenylmethoxy)-pentanoic acid;
- (R)-5-(dicyclohexylamino)-4-[(1H-indol-2-ylcarbonyl)amino]-5-oxo-pentanoic acid;
- (RS)-4-[(4-chlorophenylmethylcarbonyl)amino]-5-(dipentylamino)-5-oxo-pentanoic acid;
- (RS)-4-[(3,4-dichlorophenylmethylcarbonyl)amino]-5-(dipentylamino)-5-oxo-pentanoic acid;
- (RS)-4-[(3,4-dichlorophenylaminocarbonyl)amino]-5-(dipentylamino)-5-oxo-pentanoic acid;
- (RS)-5-(dipentylamino)-4-[(1-methyl-indol-2-ylcarbonyl) amino]-5-oxo-pentanoic acid;
- (RS)-4-[(2-benzofuran-2-ylcarbonyl)amino]-5-(dipentylamino)-5-oxo-pentanoic acid;
- (RS)-5-(dipentylamino)-4-[(2-naphthalen-2-ylcarbonyl)amino]-5-oxopentanoic acid;
- (RS)-5-(dipentylamino)-4-[(2-phenylethen-1-ylcarbonyl)amino]-5-oxopentanoic acid;
- (RS)-6-(dipentylamino)-1-ethoxy-5-[(3-methoxyphenylaminocarbonyl)amino]-6-oxo-hexanoic acid;
- (RS)-6-(dipentylamino)-5-[(3-methoxyphenylaminocarbonyl)amino]-1-pyrrolidino-6-oxo-hexanoic acid;
- (RS)-4-[(3-chlorophenylaminocarbonyl)amino]-5-(dipentylamino)-5-oxo-pentanoic acid;
- (RS)-5-(dipentylamino)-4-[(3-methoxyphenylaminocarbonyl)amino]-5-oxo-pentanoic acid; and
- (RS)-5-(dipentylamino)-1-ethoxy-4-[(3-methoxyphenylaminocarbonyl)amino]-5-oxo-pentanoic acid.

The compounds according to the present invention may be prepared by the following reaction scheme:

Synthetic Routes to Amino Acid Analogs

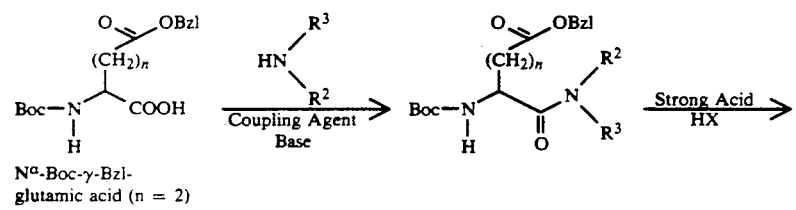

$N^\alpha$-Boc-γ-Bzl-glutamic acid (n = 2)

-continued
Synthetic Routes to Amino Acid Analogs

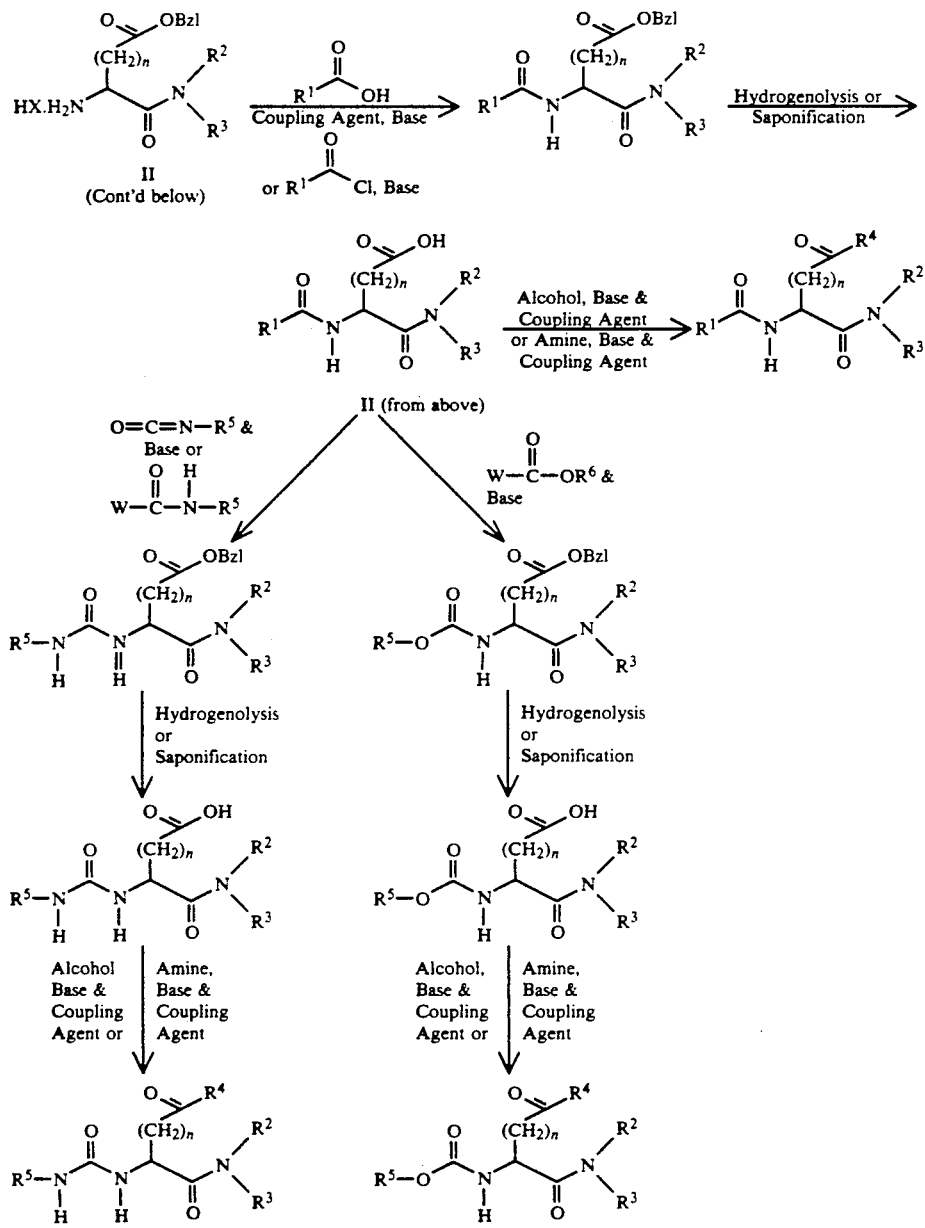

Starting with alpha-amino dicarboxylic acids, such as glutamic, aspartic, or alpha-amino acid containing a free alpha carboxyl group, an alpha-amino group suitably protected with a protecting group such as Boc, and a second carboxyl group protected with a suitable ester group, such as benzyl, the protected acid is treated with a suitable amine and a coupling agent, such as a carbodiimide (DCC, EDC), DPPA, or an alkyl chloroformate in the presence of a trialkyl amine (triethylamine, diisopropylethylamine) in a suitable solvent, such as methylene chloride, THF, or ethyl acetate.

The resultant protected amide is deprotected on the alpha-amino group by treatment with a strong acid, such as HCl in ethyl acetate, or trifluoroacetic either neat or in the presence of a solvent such as methylene chloride, which results in an alphaamino amide salt.

This alpha-amino amide salt is then either treated with a suitable acid in the presence of a coupling agent, a trialkyl amine, and a solvent, such as those mentioned above, or it is treated with a suitable acid chloride in the presence of a trialkyl amine and a solvent, such as those mentioned, above, to produce a diamide derivative. Alternatively, the alpha-amino amide salt is treated with a suitable isocyanate or activated carbamic acid derivative in the presence of a trialkyl amine and a solvent, such as those mentioned above, to produce a urea amide derivative, or it is treated with a suitable activated carbonic acid derivative in the presence of a trialkyl amine and a solvent, such as those mentioned above, to produce a carbamate amide derivative.

The diamide, urea amide, or carbamate amide derivatives are treated to remove the carboxyl protecting group, by deprotection, either with hydrogen under pressure in the presence of a suitable catalyst such as Pd/C in a solvent, such as methanol, ethanol, ethyl acetate, acetic acid, water, or in a mixture of these solvents, or by saponification with a metal hydroxide, such as NaOH in a mixture of water and an organic solvent such as THF, dioxane, or methanol. The resultant acid is finally treated with a suitable alcohol or amine in the presence of a coupling agent, a trialkyl amine, and a solvent, such as those mentioned above, to provide the compounds of Formula I.

The pharmaceutically-acceptable salts of the compounds of formula I include the conventional nontoxic salts of the compounds of formula I prepared by conventional procedures, such as treating an acid moiety of formula I with an appropriate amount of a base, such as an alkali or alkaline earth metal hydroxide, e.g., sodium, potassium, lithium, calcium, or magnesium, or an organic base, such as an amine, e.g., dibenzylethylenediamine, trimethylamine, piperidine, pyrrolidine, benzylamine and the like, or a quaternary ammonium hydroxide, such as tetramethylammonium hydroxide and the like. Generally, the salts are prepared by reacting the free acid with stoichiometric amounts of or with an excess of the desired salt-forming inorganic or organic base in a suitable solvent or in various combinations of solvents.

Screening of the novel compounds according to the present invention to determine biological activity and obtain an $IC_{50}$ value for them, in order to identify significant CCK-antagonism, may be accomplished using an $^{125}I$-CCK receptor binding assay and in vitro isolated tissue preparations. To identify significant gastrin antagonism, $^{125}I$-gastrin and $^{3}H$-pentagastrin binding assays are used. These tests involve the following:

CCK receptor binding (pancreas) method

CCK-33 was radiolabeled with $^{125}I$-Bolton Hunter reagent (2000 Ci/mmole), as described by Sankara et al. (*J. Biol. Chem.*, 254, 9349-9351, 1979). Receptor binding was performed according to Innis and Snyder (*Proc. Natl. Acad. Sci.*, 77, 6917-6921, 1980), with the minor modification of adding the additional protease inhibitors, phenylmethane sulfonyl fluoride and o-phenanthroline, which have no effect on the $^{125}I$-CCK receptor binding assay.

The whole pancreas of a male Sprague-Dawley rat (200-350 g), which had been sacrificed by decapitation, was dissected free of fat tissue and homogenized in 20 volumes of ice-cold 50 mM Tris HCl (pH 7.7 at 25° C.) with a Brinkmann Polytron PT-10. The homogenates were centrifuged at 48,000 g for 10 minutes, then the resulting pellets were resuspended in Tris Buffer, centrifuged as above, and resuspended in 200 volumes of binding assay buffer (50 mM Tris HCl, pH 7.7 at 25° C., 5 mM dithiothreitol, 0.1 mM bacitracin, 1.2 mM phenylmethane sulfonyl fluoride and 0.5 mM o-phenanthroline).

For the binding assay, 25 μl of buffer (for total binding), or unlabeled CCK-8 sulfate sufficient to give a final concentration of 1 μM of CCK-8 (for nonspecific binding), or the compounds according to the instant invention (for determination of antagonism to $^{125}I$-CCK binding) and 25 μl of $^{125}I$-CCK-33 (30,000-40,000 cpm), were added to 450 μl of the membrane suspensions in microfuge tubes. All assays were run in duplicate or triplicate, and the reaction mixtures were incubated at 37° C. for 30 minutes and centrifuged in a Beckman Microfuge (4 minutes) immediately after adding 1 ml of ice-cold incubation buffer. The supernatant was aspirated and discarded, and the pellets were counted with a Beckman Gamma 5000. For Scatchard analysis to determine the mechanism of inhibition of $^{125}I$-CCK binding by the most potent compounds (*Ann. N.Y. Acad. Sci.*, 51, 660, 1949), $^{125}I$-CCK-33 was progressively diluted with increasing concentrations of CCK-33.

CCK receptor binding (brain) Method

CCK-33 was radiolabeled and the binding was performed according to the description for the pancreas method, with modifications according to Saito et al., *J. Neurochem.*, 37, 483-490, 1981.

Male Hartley guinea pigs (300-500 g) were sacrificed by decapitation, and the brains were removed and placed in ice-cold 50 mM Tris HCl plus 7.58 g/1 Trizma-7.4 [pH 7.4 at 25° C.]. The cerebral cortex was dissected and used as a receptor source and each gram of fresh guinea pig brain tissue was homogenized in 10 ml of Tris/ Trizma buffer with a Brinkmann polytron PT-10. The homogenates were centrifuged at 42,000g for 15 minutes, then the resulting pellets were resuspended in 200 volumes of binding assay buffer (10 mM N-2-hydroxy-ethyl-piperazine-N'-2-ethane-sulfonic acid (HEPES), pH 7.7 at 25° C., 5 mM $MgCl_2$, 1 mM ethylene glycol-bis(β-amino-ethyl-ether-N,N'-tetraacetic acid (EGTA), 0.4% BSA (bovine serum albumin) and 0.25 mg/ml bacitracin, pH 6.5).

The remainder of the binding assay method was as described for the pancreas method, except that the reaction mixtures were incubated at 25° C. for 2 hours before centrifugation.

Isolated guinea pig gall bladder method

The two halves of the gall bladders, free of adjacent tissue, of male Hartley guinea pigs (400-600g), which had been sacrificed by decapitation, are suspended under 1g tension along the axis of the bile duct in 5 ml organ bath, containing a Kreb's bicarbonate solution of 118 mM NaCl, 4.75 mM KCl, 2.54 mH $CaCl_2$, 1.19 mM $KH_2PO_4$, 1.2 mM $MgSO_4$, 25 mM $NaHCO_3$ and 11 mM dextrose, which is maintained at 32° C. and bubbled with a mixture of 95% $O_2$ and 5% $CO_2$. The tissues are washed every 10 minutes for one hour to obtain equilibrium prior to the beginning of the study and the isometric contractions of the strips are recorded using Statham (60g:0.12 mm) strain gauges and a Hewlett-Packard 77588 recorder.

CCK-8 is added cumulatively to the baths and $EC_{50}$'s are determined using regression analysis. After washout (every 10 minutes for one hour), the compound to be tested is added at least 5 minutes before the addition of CCK-8 and the $EC_{50}$ of CCK-8 in the presence of compound to be tested is similarly determined.

A shift to the right of the CCK dose response curve without reduction of the maximal contractile response, indicates competitive antagonism of CCK from this method.

Isolated longitudinal muscle of guinea pig ileum

Longitudinal muscle strips with attached nerve plexus are prepared as described in *Brit. J. Pharmac.* 23: ; 356-363, 1964; *J. Physiol.* 194: 13-33, 1969. Male Hartley guinea pigs are decapitated and the ileum removed (10 cm of the terminal ileum is discarded and the adjacent 20 cm piece used) with a 10 cm piece of the ileum being stretched on a glass pipette. Using a cotton applicator to stroke tangentially away from the mesentery attachment at one end, the longitudinal muscle is separated from the underlying circular muscle and the longitudinal muscle is tied to a thread and by gently pulling, stripped away from the entire muscle. A piece of approximately 2 cm is suspended in 5 ml organ bath containing Krebs solution and bubbled with 95% $O_2$ and 5% $CO_2$ at 37° C. under 0.5 g tension. CCK-8 is added cumulatively to the baths and $EC_{50}$ values in the presence and absence of compounds to be tested is determined, as described in the gall bladder protocol above.

Gastrin Receptor Binding in Guinea Pig Gastric Glands

Guinea pig gastric mucosal glands were Prepared by the procedure of Berglingh and Obrink, *Acta Physiol. Scand.* 96: 150 (1976), with a slight modification according to Praissman et al. *C. J. Receptor Res.* 3: (1983). Gastric mucosa from male Hartley guinea pigs (300–500 g body weight) were washed thoroughly and minced with fine scissors in standard buffer consisting of the following: 130 mM NaCl, 12 mM $NaHCO_3$, 3 mM $NaH_2PO_4$, 3 mM $Na_2HPO_4$, 3 mM $K_2HPO_4$, 2 mM $MgSO_4$, 1 mM $CaCl_2$, 5 mM glucose and 4 mM L-glutamine, 25 mM HEPES at pH 7.4. The minced tissues were washed and incubated in a 37° C. shaker bath for 40 minutes, with the buffer containing 0.1% collagenase and 0.1% BSA, and bubbled with 95% $O_2$ and 5% $CO_2$. The tissues were passed twice through a 5 ml glass syringe to liberate the gastric glands, and then filtered through 200 mesh nylon. The filtered glands were centrifuged at 270 g for 5 minutes and washed twice by resuspension and centrifugation.

The washed guinea pig gastric glands were resuspended in 25 ml of standard buffer containing 0.25 mg/ml of bacitracin. For binding studies, 10 μl of buffer (for total binding) or gastrin (1 μM final concentration, for nonspecific binding) or test compound and 10 μl of $^{125}$I-gastrin (NEN, 2200 Ci/mmole, 25 pM final) or $^3$H-pentagastrin (NEN 22 Ci/mmole, 1 nM final) were added to 220 μl of gastric glands in triplicate tubes which were aerated with 95% $O_2$ and 5% $CO_2$ and capped. The reaction mixtures, after incubation at 25° C. for 30 minutes, were filtered under reduced pressure on glass G/F B filters (Whatman) and immediately washed with 4×4 ml of standard buffer containing 0.1% BSA. The radioactivity on the filters was measured using a Beckman gamma 5500 for $^{125}$I-gastrin or liquid scintillation counting for $^3$H-pentagastrin.

In Vitro Effect of Representative Compounds of Formula I on $^{125}$I-CCK-33 and Gastric Receptor Binding Compounds according to formula I competitively inhibited specific $^{125}$I-CCK-33 and gastrin receptor binding in a concentration-dependent manner as shown in Table I.

TABLE I

| | CCK Receptor Binding Results ($IC_{50}$) values in μM) | | |
|---|---|---|---|
| Compound | $^{125}$I-CCK Pancreas | $^{125}$I-CCK Brain | $^{125}$I-Gastrin |
| 1 | 250 | 800 | 900 |
| 2 | 0.018 | 2.2 | 1.7 |
| 3 | 3.7 | 88 | 17 |
| 4 | 1.1 | 47 | 34 |
| 5 | 0.0076 | 0.23 | 0.17 |
| 6 | 0.81 | 4.6 | 7.0 |
| 7 | 0.14 | 0.63 | 0.7 |

TABLE I-continued

| | CCK Receptor Binding Results ($IC_{50}$) values in μM) | | |
|---|---|---|---|
| Compound | $^{125}$I-CCK Pancreas | $^{125}$I-CCK Brain | $^{125}$I-Gastrin |
| 8 | 9.3 | 5.3 | 22 |
| 9 | 0.2 | 30 | 100 |
| 10 | 0.059 | 3.4 | 4.1 |

1. proglumide [(RS)-4-[(phenylcarbonyl)amino]-5-(dipropylamino)-5-oxo-pentanoic acid] (for comparison)
2. (RS)-4-[(3,4-dichlorophenylcarbonyl)amino]-5-(dipentylamino)-5-oxo-pentanoic acid (for comparison)
3. (S)-5-(dipropylamino)-4-[(1H-indol-2-ylcarbonyl)-amino]-5-oxo-pentanoic acid
4. (R)-5-(dipropylamino)-4-[(1H-indol-2-ylcarbonyl)-amino]-5-oxo-pentanoic acid
5. (R)-5-(dipentylamino)-4-[(1H-indol-2-ylcarbonyl)-amino]-5-oxo-pentanoic acid
6. (R)-5-(dipropylamino)-4-[(1H-indol-2-ylcarbonyl)-amino]-5-oxo-1-(phenylmethoxy)-pentanoic acid
7. (RS)-4-[(4-chlorophenylcarbonyl)amino]-5-(dipentyl-amino)-5-oxo-pentanoic acid
8. (RS)-4-[(4-chlorophenylcarbonyl)amino]-5-(dipentyl-amino)-5-oxo-1-(phenylmethoxy)-pentanoic acid
9. (R)-5-(dicyclohexylamino)-4-[(1H-indol-2-yl-carbonyl)amino]-5-oxo-1-(phenylmethoxy)-pentanoic acid
10. (R)-5-(dicyclohexylamino)-4-[(1H-indol-2-yl-carbonyl)amino]-5-oxo-pentanoic acid The ability of the amino acid derivatives of the instant invention to antagonize CCK and gastrin makes these compounds useful as pharmaceutical agents for mammals, especially for humans, for the treatment and prevention of disorders wherein CCK and/or gastrin may be involved. Examples of such disease states include gastrointestinal disorders, especially such as irritable bowel syndrome or ulcers, excess pancreatic or gastric secretion, acute pancreatitis, or motility disorders; central nervous system disorders, caused by CCK interactions with dopamine, such as neuroleptic disorders, tardive dyskinesia, Parkinson's disease, psychosis or Gilles de la Tourette Syndrome; disorders of appetite regulatory systems; Zollinger-Ellison syndrome, antral G cell hyperplasia, or pain (potentiation of opiate analgesia).

The compounds of the instant invention or pharmaceutically-acceptable salts thereof, may be administered to a human subject either alone or, preferably, in combination with pharmaceuticallyacceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

When a compound according to the instant invention, or a salt thereof, is used as an antagonist of CCK or gastrin in a human subject, the daily dosage will normally be determined by the prescribing physician. Moreover, the dosage will vary according to the age, weight, and response of the individual patient, as well as the severity of the patient's symptoms. However, in most instances, an effective daily dosage will be in the range of from about 0.05 mg/kg to about 50 mg/kg of body weight, and preferably, of from 0.5 mg/kg to about 20 mg/kg of body weight, administered in single or divided doses In some cases, however, it may be necessary to use dosages outside these limits.

The invention is further defined by reference to the following examples which are intended to be illustrative and not limiting.

EXAMPLE 1

Synthesis of (S)-5-(dipropylamino)-4-[(1H-indol-2-ylcarbonyl)amino]-5-oxo-1-(phenylmethoxy)-pentanoic acid A. $N^\alpha$-Boc-$\gamma$-Bzl-glutamic acid dipropylamide ate (NaHCO₃), dried over anhydrous sodium sulfate and evaporated, with the residue being purified by silica gel flash chromatography, eluting with chloroform.

B. $\gamma$-Bzl-glutamic acid dipropylamide.HCl

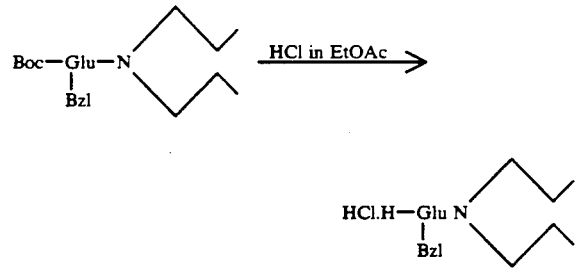

The purified $N^\alpha$-Boc-$\gamma$-Bzl-glutamic acid dipropylamide of Step A was dissolved in 30 ml of ethyl acetate and cooled to −25° C. Hydrogen chloride gas was added to the solution until the saturation point was reached and the temperature of the solution was allowed to rise for 30 minutes to 0° C. Nitrogen was then flushed through the solution, followed by evaporation to give a clear yellow residue that contained some solvent.

C. (S)-5-(dipropylamino)-4-[(1H-indol-2-ylcarbonyl)amino]-5-oxo-1-(phenylmethoxy)-pentanoic acid ($N^\alpha$-indole-2-carbonyl-$\gamma$-benzyl-glutamic acid dipropylamide)

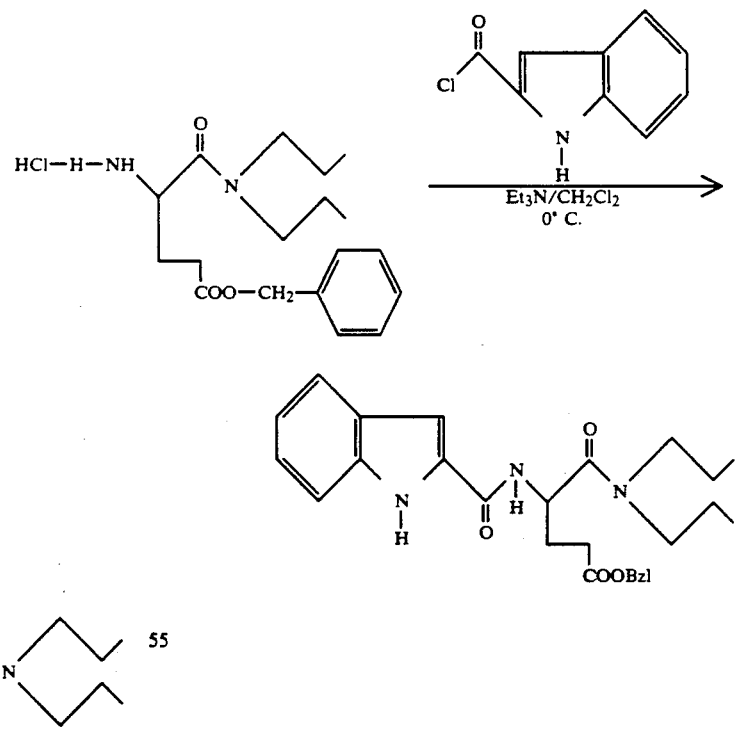

1.35 g (4.0 mmol) of $N^\alpha$-Boc-$\gamma$-Bzl-L-glutamic acid was dissolved in methylene chloride and 0.45 g (4.4 mmol) of di-n-propylamine and 0.843 g (4.4 mmol) of 1-(3-dimethylaminopropyl)-3-ethylcarbodiimide hydrochloride (EDC) was added to it. The pH of the solution was brought to about 8 with triethylamine (Et₃N) and the solution was stirred until no further reaction was observed by TLC. The reaction solution was then extracted with 0.5M citric acid and 1N sodium bicarbon- The clear yellow residue from Step B, was dissolved in methylene chloride, and the solution was cooled to about 0° C. 0.72 g of indole-2-carbonyl chloride was added, followed by 1 ml of triethylamine, and after stirring for 45 minutes, the mixture was filtered and purified on a silica gel flash chromatography column, with chloroform as the elution solvent.

EXAMPLE 2

Synthesis of
(S)-5-(dipropylamino)-4-[(1H-indol-2-yl-carbonyl-)amino]-5-oxo-pentanoic acid

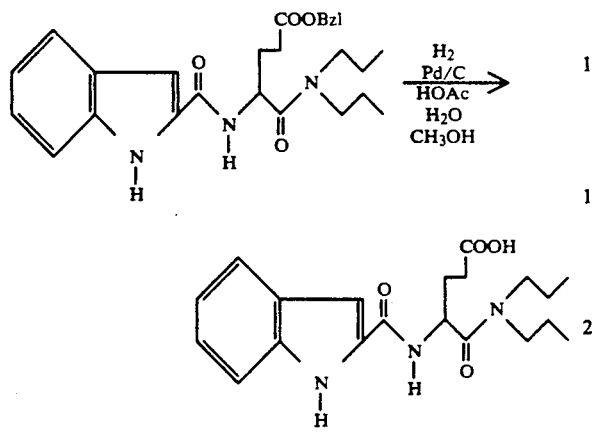

The product from the combined chromatography fractions from Step C of Example 1 was dissolved in ml of methanol, a solution of 50% aqueous acetic acid (7.5 ml) was added, and the combined solution was added to 100 mg of palladium-on-carbon catalyst in a small shaker flask and shaken with $H_2$ overnight. The solvent was evaporated and the residue was dissolved in ethyl acetate, then precipitated with petroleum ether, giving a solid which was purified by silica gel flash chromatography with 97:3 chloroform/methanol as the elution solvent, to give 115.3 mg of product.

NMR-consistent with expected structure.
Elemental analysis: $C_{20}H_{27}N_3O_4 \cdot 0.25H_2O$:
Calculated: 11.12, N; 63.55, C; 7.33, H.
Found: 11.18, N; 63.43; C, 7.45, H.

EXAMPLE 3

Synthesis of
(R)-5-(dipropylamino)-4-[(1H-indol-2-yl-carbonyl-)amino]-5-oxo-1-(phenylmethyloxy) -pentanoic acid

A. $N^\alpha$—Boc-$\gamma$-Bzl—D-glutamic acid dipropylamide

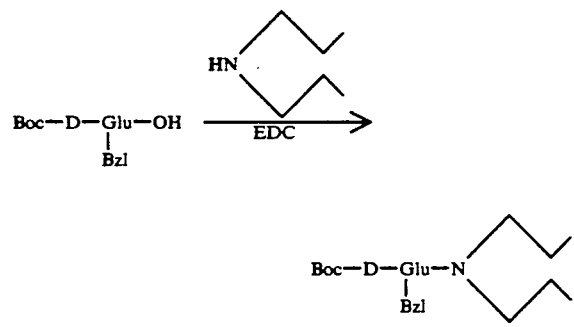

$N^\alpha$-Boc-$\gamma$-Bzl-D-glutamic acid was used as the starting material in the process described in Step A of Example 1.

B. $\gamma$-Bzl—D-glutamic acid dipropylamide·HCl

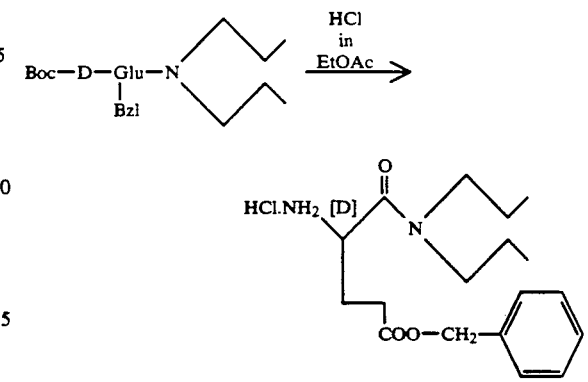

The purified $N^\alpha$-Boc-$\gamma$-Bzl-D-glutamic acid dipropylamide of Step A was dissolved in ethyl acetate and cooled to 25° C. in a dry ice/2-propanol bath. Nitrogen was bubbled into the solution until a nitrogen atmosphere was achieved, and hydrogen chloride gas was bubbled into the solution until the saturation point was reached. After stirring for 20 minutes at −25° C., nitrogen was flushed through the solution, and the solution was evaporated to give a clear yellow residue.

C. (R)-5-(dipropylamino)-4-[(1H-indol-2-yl-carbonyl)amino]-5-oxo-1-(phenylmethoxy)-pentanoic acid

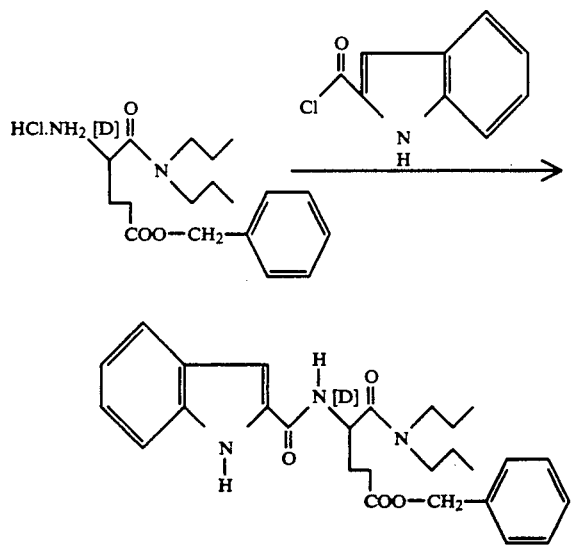

The clear yellow residue of Step B was dissolved in about 15 ml of methylene chloride, and the solution was cooled to about 0° C., after which 0.72g of indole-2-carbonyl chloride was added. About 1 ml of triethylamine was added, the pH was adjusted to between 9 and 10, and the reaction was stirred overnight, after which the reaction mixture was charged onto a silica gel flash chromatography column, which was eluted with chloroform, with fractions 1 through 18 being collected and combined.

Analysis for $C_{27}H_{33}N_3O_4$:
Calculated: 69.95, C; 7.18, H; 9.07, N.
Found: 70.22, C; 7.42, H; 9.01, N.
NMR-consistent with expected structure.

EXAMPLE 4

Synthesis of (R)-5-(dipropylamino)-4[(1H-indol-2-ylcarbonyl-)amino)]-5-oxo-pentanoic acid The product from Example 3 was dissolved in 30 ml of methanol, and a solution of 7.5 ml of 50% aqueous acetic acid was added. This solution, in turn, was added to 100 mg of Pd/C in a small Parr shaker flask, from which the air was evacuated, and the mixture was shaken under H₂ on a Parr shaker overnight, before the mixture was filtered and the solvent was evaporated. The residue was dissolved in acetone, then brought to the cloud point with hexane, with crystals beginning to form after about an hour at room temperature. The mixture was then stored at 0° C. for four days, after which the crystals were filtered and analyzed.

Yield: 474 mg, mp 133-136° C.
Analysis for C₂₀H₂₇N₃O₄.0.4 C₃H₆O:
Calculated: 10.61, N; 64.26, C; 7.48, H.
Found: 10.60, N; 64.32, C; 7.63, H.
NMR Consistent with expected structure.
Mass spectrum-molecular ion observed at m/z 373.

EXAMPLE 3

Synthesis of (R)-5-(dipentylamino)-4-[(1H-indol-2-ylcarbonyl-)amino]-5-oxo-pentanoic acid A. Nα—Boc-γ-Bzl—D-glutamic acid dipentylamide

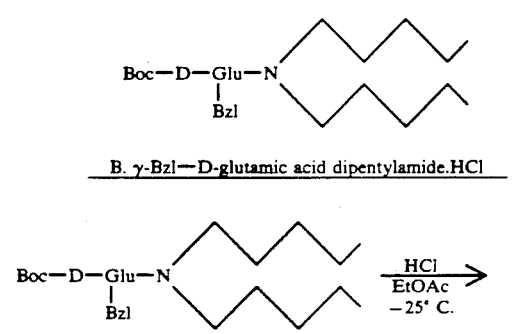

Employing the process of Step A of Example 1, 1.35g of Nα-Boc-γ-Bzl-D-glutamic acid, 0.843 g of EDC and 0.692 g (0.89 ml) of dipentyl amine were used as reagents, with the reaction mixture being purified on a silica gel column with chloroform as the elution solvent. Fractions 3 through 7 were combined and evaporated, resulting in 0.92 g of product, B. γ-Bzl—D-glutamic acid dipentylamide.HCl

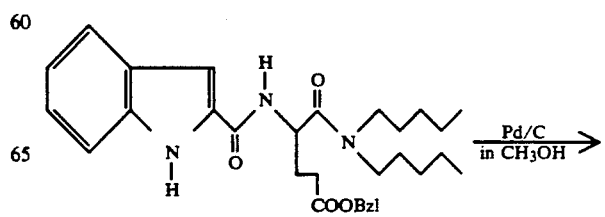

The oil from Step A (0.92g, 1.87 mmol) was dissolved in 60 ml of ethyl acetate and deblocking was carried out as described in Step B of Example 1. The solution was then flushed with nitrogen and evaporated to an oily residue.

C. Nα-indole-2-carbonyl-γ-Bzl—D-glutamic acid dipentylamide

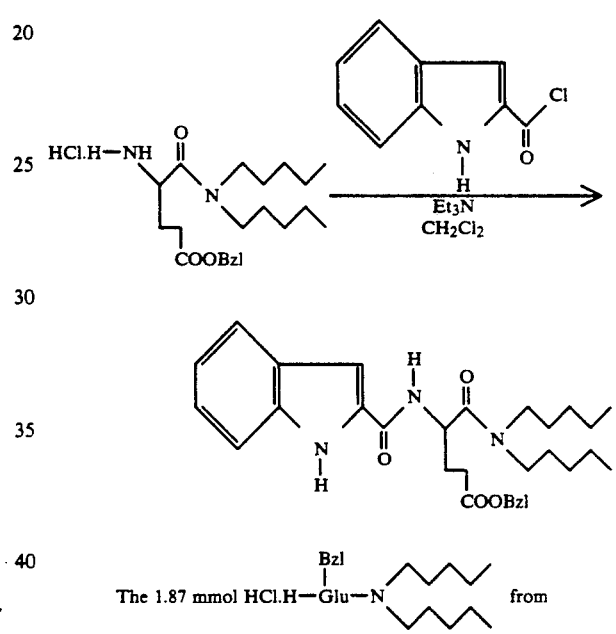

Step B was dissolved in methylene chloride at 0° C. and 2-indole carbonyl chloride (0.37 g, 2.05 mmol) was added. After stirring for about 2 min., 1 ml triethyl amine was added to bring the pH of the solution up to about 8. The reaction solution was stirred at room temperature overnight, then chromatographed on silica gel which was eluted with chloroform. Fractions 29 through 33 were combined and the chloroform was evaporated.

D. (R)-5-(dipentylamino)-4-[(1H-indol-2-ylcarbonyl)amino]-5-oxo-pentanoic acid

-continued

D. (R)-5-(dipentylamino)-4-[(1H-indol-2-ylcarbonyl)amino]-5-oxo-pentanoic acid

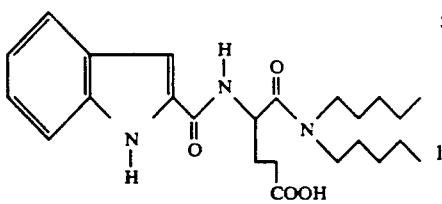

The combined chromatography fractions from Step C were dissolved in 30 ml of methanol and 7.5 ml of a solution of 50% aqueous acetic acid (7.5 ml) was added. This solution was added to 100 mg of Pd/C catalyst in a small Parr bottle an the mixture was hydrogenated on a Parr shaker apparatus for 5 hours, after which the reaction was filtered through super cel and evaporated. The residue was dissolved in ether and petroleum ether was added to precipitate a wine colored solid, which was washed and filtered twice using petroleum ether until little color remained. Additional petroleum ether was added, and a white solid which was dissolved in ether was placed on a 2000 μ Prep TLC plate, and developed in 92:8 $CHCl_3$-methanol.

Yield 214.8 mg. mp 115–123°.
NMR Consistent.
Elemental Analysis for $C_{24}H_{35}N_3O_4 \cdot 0.511K$
Calculated: 64.15, C; 7.65, H; 9.35, N.
Observed: 64.05, C; 7.84, H; 9.33, N.

EXAMPLE 6

Synthesis of (RS)-4-[(4-chlorophenylaminocarbonyl)amino]-5-(dipentylamino)-5-oxo-1-(phenylmethyloxy) pentanoic acid A. $N^\alpha$Boc-γ-Bzl-DL-glutamic acid dipentylamide

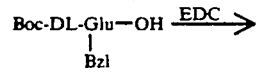

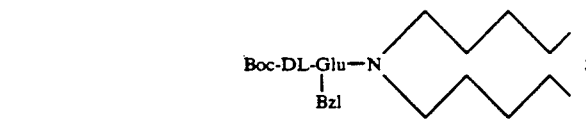

This synthesis was carried out with 1.35 g (4 mmol) $N^\alpha$-Boc-γ-Bzl-DL-glutamic acid, 0.843 g (4.4 mmol) EDC, and 0.89 ml (0.692 g, 4.4 mmol) dipentylamine as reagents according to the procedures of Step A of Example 5. The product was purified by silica gel chromatography B. γ-Bzl-DL-glutamic acid dipentylamide.HCl

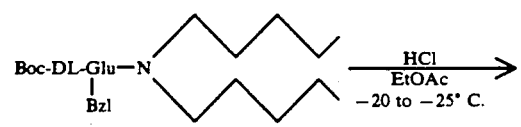

-continued

B. γ-Bzl-DL-glutamic acid dipentylamide.HCl

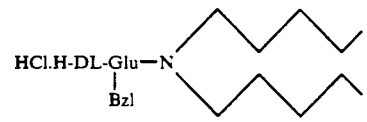

The purified product from Step A was dissolved in 60 ml of ethyl acetate, and deblocking was carried out as described in Step B of Example 5. The deblocking solution was flushed with nitrogen, and the HCl-solution was evaporated to a residue. Yield 0.6 g.

C. (RS)-4-[(4-chlorophenylaminocarbonyl)amino]-5-(dipentylamino-5-oxo-1-(phenylmethyloxy)-pentanoic acid

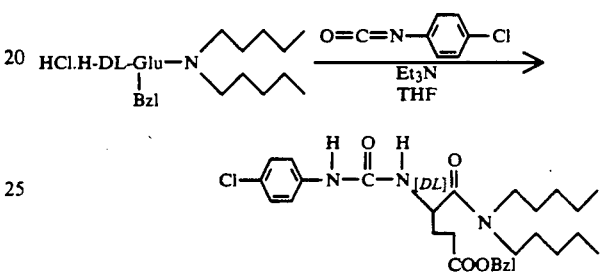

The residue from the Step B (0.6g, 1.45 mmol) was dissolved in dry THF (25 ml), triethylamine was added to neutralize the HCl salt, and 0.223 g (1.45 mmol) p-chlorophenylisocyanate was added. The reaction was protected from moisture and stirred at room temperature for 24 hrs., after which the reaction mixture was placed on a silica gel column and purified by flash chromatography. The product fractions were combined and evaporated.

Yield 640 mg. NMR consistent.
Analysis for $C_{29}H_{40}ClN_3O_4$:
Calculated: 7.92, N; 65.70, C; 7.60, H.
Found: 7.54, N; 65.58, C; 7.73, H.

EXAMPLE 7

Synthesis of (RS)-4-[(4-chlorophenylaminocarbonyl)-amino-5-(dipentylamino)-5-oxo-pentanoic acid

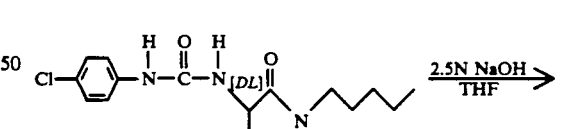

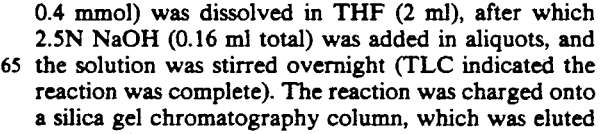

The benzylester from Step C of Example 6 (210 mg, 0.4 mmol) was dissolved in THF (2 ml), after which 2.5N NaOH (0.16 ml total) was added in aliquots, and the solution was stirred overnight (TLC indicated the reaction was complete). The reaction was charged onto a silica gel chromatography column, which was eluted with the following solvent systems: 200 ml, chloroform, 200 ml 97:3 CHCl₃-methanol, 200 ml 95:5 CHCl₃-methanol, and 200 ml 90:10 CHCl₃-methanol. Fractions 9 through 15 were combined and evaporated, but showed some impurity at the origin.

The residue obtained after evaporation was further purified on a 2000 μ prep TLC plate, and the product was isolated and dried.

Analysis for C₂₂H₃₄ClN₃O₄.0.85 CH₃OH.
Calculated: 8.99, N; 58.73, C; 8.06, H.
Found: 8.79, N; 58.42, C; 7.66, H.
NMR Consistent.

EXAMPLE 8

Synthesis of
(RS)-5-(dicyclohexylamino)-4-[(1H-indol-2-ylcarbonyl)amino]-5-oxo-1-(phenylmethyloxy) -pentanoic acid

A. N^α-Boc-γ-Bzl-D-glutamic acid

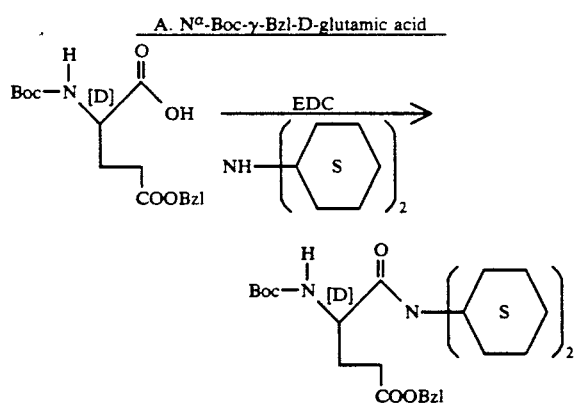

This synthesis was carried out according to the procedure of Example 5 using the following quantities of reagents: 1.35 g (4 mmol) N^α-Boc-γ-benzyl-D-glutamic acid; 0.843 g (4 mmol) EDC; and 1.02 ml (0.725 g, 4 mmol) dicyclohexylamine.

Instead of purification by chromatography, the mixture was filtered then extracted with 5M citric acid and 1N sodium bicarbonate. The solution was dried over sodium sulfate, then evaporated to an oil, which crystalized on standing.

B. γ-Bzl-D-glutamic acid dicyclohexylamide.HCl

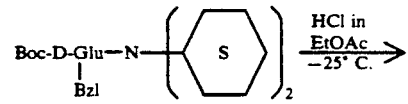

B. γ-Bzl-D-glutamic acid dicyclohexylamide.HCl

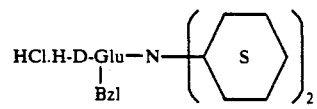

The solid obtained from Step A was dissolved in 60 ml of ethyl acetate, and the deblocking was carried out as described in Example 7. The deblocking solution was flushed with nitrogen and evaporated to a beige solid. This solid was used in the next reaction.

C. (RS)-5-(dicyclohexylamino)-4-[(1H-indol-2-yl-carbonyl)amino]-5-oxo-1-(phenylmethoxy)-pentanoic acid

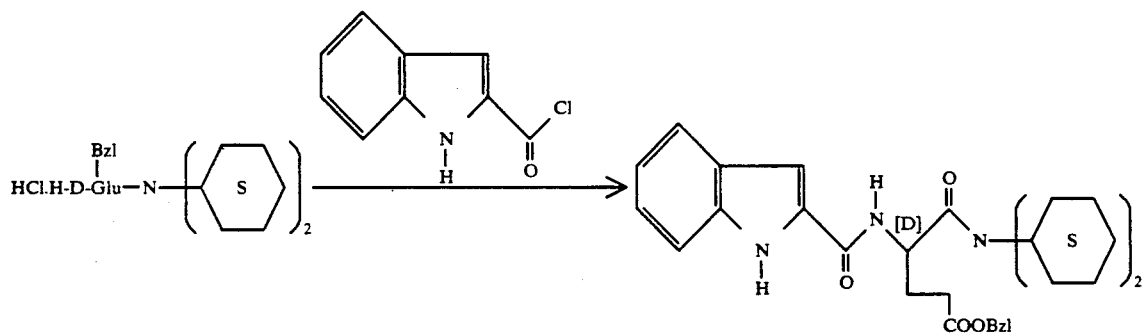

The product from Step B was dissolved in methylene chloride at 0° C. and 2-indole carboyl chloride was added. After stirring for about 2 minutes, triethyl amine was added to bring the pH of the solution up to about 8, and the reaction solution was stirred at room temperature overnight, and chromatographed on silica with a chloroform-andhexane solvent system. The resultant product was further purified by preparative TLC and that product was crystalized from chlorofrom-petroleum ether, and it was washed with ether and dried.

Analysis for C₃₃H₄₁N₃O₄.
Calculated: 7.72, N; 72.90, C; 7.60, H.
Found: 7.79, N; 72.64, C; 7.54, H.
NMR Consistent.

EXAMPLE 9

Synthesis of
(R)-5-(dicyclohexylamino)-4[(1H-indol-2-ylcarbonyl)amino]-5-oxo-pentanoic acid

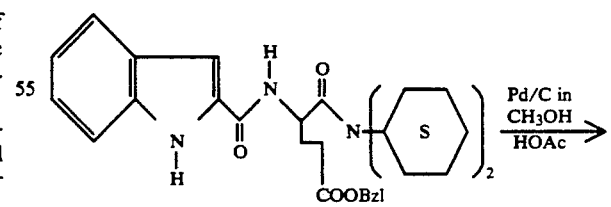

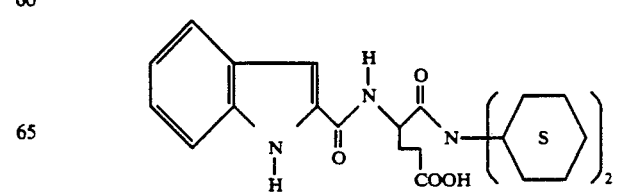

The product from Example 8 was dissolved in 35 ml of methanol and 8.75 ml of a solution of 50% aqueous acetic acid wa added. This solution was added to 100 mg of Pd/C catalyst in a small Parr bottle, and the mixture was placed on a Parr shaker apparatus for 5 hours. The reaction was filtered through Super Cel with the filtering agent and catalyst being washed with methanol, followed by chloroform, and the solution was evaporated to a white solid. The solid was then suspended in methanol to which ether was added, and the resultant mixture was filtered, and the product dried for 20 hours.

Analysis for $C_{26}H_{35}N_3O_4.0.651K$:
Calculated: 8.77, N; 65.18, C; 7.36, H.
Found: 8.47, N; 65.38, C; 7.27, H.
NMR Consistent Mass spectrum (FAB) M+H=454.

What is claimed is:

1. A compound of the formula:

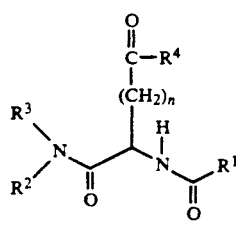
(I)

wherein $R^1$ is $(CH_2)_m$—$R^5$ or $X^1$—$(CH_2)_m$—$R^6$;

$R^2$ and $R^3$ are independently selected form H; $C_1$-$C_8$-straight- or branched-chain-alkyl; $C_3$-$C_8$-cycloalkyl; phenyl; benzyl; mono- or dihalophenyl; and mono- or dihalobenzyl; with the proviso that $R^2$ and $R^3$ cannot both be H concurrently;

$R^4$ is OH; $C_1$-$C_4$-straight- or branched-chainalkoxy; $C_3$-$C_6$-cycloalkyl; $OCH_2$-phenyl; amino-mono- or di-$C_1$-$C_4$-straight-or branched-chain-alkyl; amino-mono- or di-$C_3$-$C_6$-cycloalkyl; NH—$CH_2$-phenyl;

$R^5$ is

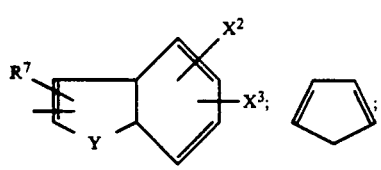

$R^6$ is α- or β-naphthyl;

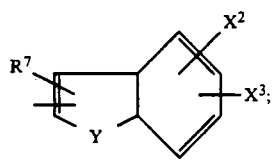

mono- or di-substituted- or unsubstituted-phenyl, where the substituents are selected from halo; $NO_2$; OH; $CF_3$; CN; $C_1$-$C_4$-straight- or branched-chain-alkyl; $C_1$-$C_4$-straight- or branched-chain-alkyloxy; $C_1$-$C_4$-straight- or branched-chain-alkylthio;

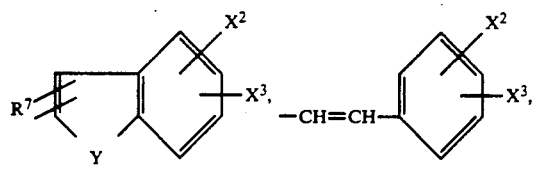

$R^7$ is H; $C_1$-$C_4$-straight- or branched-chain-alkyl;
$X^1$ is O or NH;
$X^2$ and $X^3$ are independently H; OH; $NO_2$; halo; $C_1$-$C_4$-straight- or branched-chain-alkyl; $C_1$-$C_4$-straight- or branched-chain-alkylthio; or $C_1$-$C_4$-straight-or branched-chain-alkoxy;
$X^4$ is O or HH;
Y is O
n is 1 to 3;
m is 0 to 4;
halo is F, Cl, Br, or I;
or a pharmaceutically acceptable salt thereof.

2. A compound according to claim 1, wherein $R^2$ and $R^3$ are independently —$(CH_2)_{3-5}$—$CH_3$, benzyl or mono- or dihalobenzyl; $R^4$ is OH, $C_1$-$C_4$-straight- or branched-chain-alkoxy, $OCH_2$-phenyl, amino-mono- or di-$C_1$-$C_4$-straight-or branched-chain-alkyl; NH—$CH_2$-phenyl;

$R^5$ is

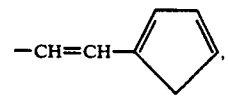

$R^6$ is α- or β-naphthyl,

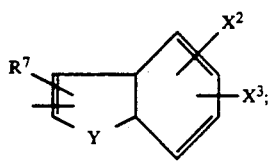

or mono- or di-substituted or unsubstituted-phenyl, where the substituent(s) are selected from halo, $CF_3$, $C_1$-$C_4$-straight- or branched-alkyl, $C_1$-$C_4$-straight- or branched-alkoxy, and $C_1$-$C_4$-straight-or branched-alkylthio; $R^7$ is H; $X^2$ and $X^3$ are independently H, halo, $C_1$-$C_4$-straight-or branched-alkylthio or $C_1$-$C_4$-straight or branched-alkoxy; Y is 0; n is 2 or 3; and m is 0 or 1.

3. A compound according to claim 1 wherein $R^1$ is $(CH_2)_m$—$R^5$; $R^2$ and $R^3$ are independently $(CH_2)_{3-5}$—$CH_3$; $R^4$ is OH; $R^5$ is $R^7$ is H; $X^2$ and $X^3$ are independently H or halo; Y is 0; n is 2 and m is 0.

4. A compound according to claim 1, wherein $R^1$ is $X^1-(CH_2)_m-R^6$; $R^2$ and $R^3$ are independently $(CH_2)_{3-5}-CH_3$; $R^4$ is $C_1-C_4$-straight- or branched-chain-alkoxy, $OCH_2$-phenyl, amino-mono- or di-$C_1-C_4$-straight-or branched-chain-alkyl, $NH-CH_2$-phenyl; $R^6$ is α-or β-naphthyl,

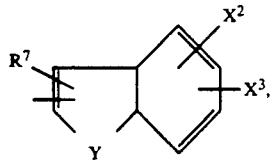

unsubstituted or mono- or disubstituted phenyl, where the substituent is halo, $C_1-C_4$-straight-or branched-chain-alkoxy, $C_1-C_4$-straight-or branched-chain-alkoxy,

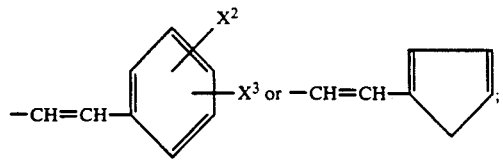

$R^7$ is H; $X^1$ is NH; $X^2$ and $X^3$ are independently H or halo; Y is 0; n is 2 or 3 and m is 0.

(RS)-4-[(2-benzofuran-2-ylcarbonyl)amino]-5-(dipentylamino)-5-oxo-pentanoic acid.

5. A compound according to claim 1 which is (RS)-4-[(2-benzofuran-2-ylcarbonyl)amino]-5-(dipentylamino)-5-oxo-pentanoic acid.

* * * * *